(12) United States Patent
Torgue et al.

(10) Patent No.: US 10,020,086 B2
(45) Date of Patent: Jul. 10, 2018

(54) METHOD AND APPARATUS FOR THE PRODUCTION OF LEAD 212 FOR MEDICAL USE

(71) Applicant: Orano Med, Courbevoie (FR)

(72) Inventors: Julien Torgue, Gaithersburg, MD (US); Patrick Maquaire, Tourlaville (FR); John Young, Woodridge, IL (US); Gilbert Andreoletti, Equeurdreville (FR); Patrick Bourdet, Kensington, MD (US)

(73) Assignee: Orano Med, Courbevoie (FR)

( * ) Notice: Subject to any disclaimer, the term of this patent is extended or adjusted under 35 U.S.C. 154(b) by 549 days.

(21) Appl. No.: 14/402,325

(22) PCT Filed: May 23, 2013

(86) PCT No.: PCT/EP2013/060672
§ 371 (c)(1),
(2) Date: Nov. 20, 2014

(87) PCT Pub. No.: WO2013/174949
PCT Pub. Date: Nov. 28, 2013

(65) Prior Publication Data
US 2015/0170776 A1 Jun. 18, 2015

(30) Foreign Application Priority Data

May 24, 2012 (FR) .................................. 12 54798

(51) Int. Cl.
| | |
|---|---|
| *G21G 1/00* | (2006.01) |
| *A61K 51/12* | (2006.01) |
| *C22B 13/02* | (2006.01) |
| *C22B 13/06* | (2006.01) |
| *C22C 11/00* | (2006.01) |
| *G21G 4/08* | (2006.01) |

(52) U.S. Cl.
CPC ........... *G21G 1/0005* (2013.01); *A61K 51/12* (2013.01); *C22B 13/02* (2013.01); *C22B 13/06* (2013.01); *C22C 11/00* (2013.01); *G21G 4/08* (2013.01); *G21G 2001/0094* (2013.01)

(58) Field of Classification Search
CPC .... B01D 15/08–15/345; B01D 15/40–15/428; G21G 4/08
USPC .......................... 423/2; 250/432 PD; 252/645
See application file for complete search history.

(56) References Cited

U.S. PATENT DOCUMENTS

| | | | | |
|---|---|---|---|---|
| 4,663,129 | A | | 5/1987 | Atcher et al. |
| 5,038,046 | A | * | 8/1991 | Norman ............. A61K 51/1282 250/432 PD |
| 6,126,909 | A | * | 10/2000 | Rotmensch ........ A61K 51/1282 210/682 |
| 6,787,042 | B2 | * | 9/2004 | Bond ....................... B01J 39/04 210/143 |

FOREIGN PATENT DOCUMENTS

WO 2005079867 A2 9/2005

OTHER PUBLICATIONS

Horwitz, et al., "A lead-selective extraction chromatographic resin . . . geological samples" Analytica Chimica Acta, 292(3), 1994, pp. 263-273.*
Al Mahamid et al., "Rapid Separation . . . Liquid Ion Chromatography" J. Radioanal. Nucl. Chem., Letters 127(5), pp. 357-365, 1988.*
Atcher, R., et al., "An improved generator for the production of 212Pb and 212Bi from 224Ra", "Int. J. Rad. Appl. Instrum. A.", 1988, pp. 283-286, vol. 39, No. 4.
Azure, M., et al., "Radiolabeling and Imaging of 212Pb-TCMC-Transtuzumab", World Molecular Imaging Congress, Sep. 8-11, 2010, p. 1, Presentation No. 0887B, Poster Session 4c: In Vivo Studies & Development/Novel Use of Imaging Probes, Location: Kyoto, Japan.
Horak, E., et al., "Radioimmunotherapy targeting of HER2/neu oncoprotein on ovarian tumor using lead-212-DOTA-AE1", "The Journal of Nuclear Medicine", Dec. 1997, pp. 1944-1950, vol. 38, No. 12.
Milenic, D., et al., "Alpha-particle radioimmunotherapy of disseminated peritoneal disease using a (212)Pb-labeled radioimmunoconjugate targeting HER2", "Cancer Biotherapy & Radiopharmaceuticals", Oct. 2005, pp. 557-568, vol. 20, No. 5.
Narbutt, J., et al., "Gamma emitting radiotracers 224Ra, 212Pb and 212Bi from natural thorium", "Applied Radiation and Isotopes", Jan.-Feb. 1998, pp. 89-91, vol. 49, Nos. 1-2.
NOTE: For the non-patent literature citations that no month of publication is indicated, the year of publication is more than 1 year prior to the effective filing date of the present application.

* cited by examiner

*Primary Examiner* — Steven J Bos
(74) *Attorney, Agent, or Firm* — Alston & Bird, LLP

(57) ABSTRACT

The invention relates to a method for preparing lead (212) for medical use. This method comprises the production of lead (212) by the decay of radium (224) in a generator comprising a solid medium to which the radium (224) is bound, followed by the extraction of the lead (212) from the generator in the form of an aqueous solution A1, characterized in that the lead (212) contained in the aqueous solution A1 is purified from the radiological and chemical impurities, also contained in said aqueous solution, by a liquid chromatography on a column. The invention also relates to an apparatus specially designed for automated implementation in a closed system of said method. It further relates to lead (212) produced by means of this method and this apparatus. Applications: manufacture of radiopharmaceuticals based on lead (212), useful in nuclear medicine for the treatment of cancers, particularly by a-radioimmunotherapy, or for medical imaging, in both humans and animals.

12 Claims, 2 Drawing Sheets

METHOD AND APPARATUS FOR THE PRODUCTION OF LEAD 212 FOR MEDICAL USE

CROSS-REFERENCE TO RELATED APPLICATIONS

This application is a U.S. national phase under the provisions of 35 U.S.C. § 371 of International Patent Application No. PCT/EP13/60672 filed May 23, 2013, which in turn claims priority of French Patent Application No. 1254798 filed May 24, 2012. The disclosures of such international patent application and French priority patent application are hereby incorporated herein by reference in their respective entireties, for all purposes.

TECHNICAL FIELD

This invention relates to the field of radionuclide production for medical use.

More specifically it relates to a method for producing lead 212 that has a very high degree of radiological, chemical and even bacteriological purity, making it perfectly suited to medical use, as well as to an apparatus specially designed for automated implementation in a closed system of this method.

It also relates to lead 212 produced by means of this method and this apparatus.

Thus, the invention is especially likely to find applications in the manufacture of radiopharmaceuticals (or radiotracers) based on lead 212, useful in nuclear medicine whether for the treatment of cancers, particularly by α-radio-immunotherapy, or for medical imaging, in both humans and animals.

STATE OF THE PRIOR ART

Lead 212 is a rare radioactive isotope of lead. For several years now, it has been the subject of promising research, notably in the treatment by α-radio-immunotherapy of cancers and, in particular, cancer of the pancreas, ovaries, colon, breast and prostate (see for example Milenic et al., *Cancer Biotherapy and Radiopharmaceuticals* 2005, 20 (5), 557-568, reference 111).

Lead 212 is also a radioelement that has been shown to be of benefit in medical imaging, particularly for monophoton emission tomography coupled to a scan (Azure et al., World Molecular Imaging Congress, 8-11 Sep. 2010, Kyoto, reference PD.

In both cases, the use of lead 212 involves its injection into the patient in the form of a radiopharmaceutical, in other words of a product in which it is bound, typically by the intermediary of a chelating agent, to a molecule capable of highly specific targeting the cells to be destroyed (in the case of radioimmunotherapy) or to be observed (in the case of medical imaging), such as an antibody.

To this end, lead 212 must comply with extremely rigorous requirements concerning quality and, especially, radiological (this should ideally be at least equal to 99.95%), chemical and bacteriological purity.

As illustrated in FIG. 1 attached in the appendix, which represents the radioactive decay chain of thorium 232, lead 212 belongs to the thorium 232 radioactive family of which it is a daughter product. It is also a daughter product of radium 224 which, in this chain, falls between thorium 232 and lead 212.

Lead 212, which is currently being experimented on for medical purposes, is obtained using a radium 224 generator, in other words a device containing a solid medium, typically a cation exchange resin, to which radium 224 is bound, and by means of a method which consists in allowing this radium to produce lead 212 by radioactive decay, recovering the lead 212 by elution, and by submitting the eluate containing this lead to a series of acid digestions in order to reduce the quantity of chemical impurities it contains and, in particular, impurities resulting from radiolysis of the solid medium present in the generator (see for example Horak et al., *Journal of Nuclear Medicine* 1997, 38, 1944-1950, reference 131; U.S. Pat. No. 4,663,129, reference 141).

However this method does not systematically guarantee the production of lead 212 with radiological purity consistently greater than 99.50%.

It also does not make it possible to carry out true chemical purification of the lead 212.

Moreover, the acid digestions applied, which consist in putting lead 212 in a highly concentrated aqueous solution of a strong acid, for example hydrochloric or nitric acid, then evaporating this acid, are carried out manually under a hood and require about an hour-and-a-half of handling. Yet the half-life (also called period) of lead 212 is only 10.6 hours.

It would therefore be desirable, within the scope of producing lead 212 for medical use at an industrial or hospital scale (that is to say in nuclear medicine departments), to have a lead 212 production method that:

(1) guarantees that the lead 212 produced has radiological purity at least equal to 99.95%;

(2) also guarantees that the lead 212 has greater chemical purity than that of lead 212 produced by the methods of the current state of the art;

(3) makes it possible to produce lead 212 more quickly than the method of the current state of the art, given its relatively short half life; and (4) can be automated, or at least allows the number of manual operations that need to be carried out to be reduced to a minimum, and can be implemented in a closed system in order to limit the risk of contaminating staff in charge of this production, as well as the products to be administered to the patients.

It would also be desirable to have available an apparatus that makes it possible to implement this method in an automated manner and in a closed system.

Finally, it would be desirable to have a method and apparatus that can be industrialised.

The invention specifically proposes a method for producing lead 212 for medical use which fulfils all these requirements, as well as an apparatus specially designed for automated implementation in a closed system of this method.

DESCRIPTION OF THE INVENTION

A first subject-matter of the invention is a method for producing lead 212 for medical use which comprises the production of lead 212 by the decay of radium 224 in a generator containing a solid medium to which radium 224 is bound, and the extraction of this lead from the generator in the form of an aqueous solution A1, and which is characterised in that it further comprises a radiological and chemical purification of the lead 212 contained in said aqueous solution A1 which is carried out by a liquid chromatography on a column.

Thus according to the invention, once extracted from the radium 224 generator, the lead 212 is subjected to a liquid chromatography on a column. This makes it possible to eliminate very efficiently both radiological and chemical impurities, which are extracted from the generator jointly with the lead 212, and therefore to obtain lead 212 presenting a radiological purity and a chemical purity that have never been achieved to date, or at least that have never yet been described in the literature.

The radiological impurities are the radioelements likely to be present in the radium 224 generator, starting with the latter, whereas the chemical impurities are the organic degradation products resulting from radiolysis of the solid medium onto which the radium 224 is bound in the generator, if this solid medium is organic, as well as the organic and mineral contaminants likely to be introduced into this generator, for example by the solutions that are used to prepare and extract the lead 212.

In addition to producing lead 212 that is both radiologically and chemically extremely pure, the use of a liquid chromatography on a column to purify the lead 212 after its extraction from the radium 224 generator also makes it possible to produce lead 212 more quickly than the method of the current state of the art.

Moreover, as the liquid chromatography on a column is a technique that can be automated and coupled to the production of lead 212 by a radium 224 generator, which is itself a technique that can be automated, this means it offers a method for the production of lead 212 that can be implemented in an automated mode.

In addition, as the liquid chromatography on a column and the production of lead 212 by a radium 224 generator are techniques based on the circulation of liquid media through solid media, they can both be implemented in a closed system.

In the preceding and subsequent paragraphs, the term "liquid chromatography on a column" refers to any chromatography in which the mobile phase is a liquid phase and the stationary phase, or immobilized phase, is contained in a column, in other words a tube in which the mobile phase moves under the effect of gravity or under the effect of pressure.

Moreover, the term "radiological purity" refers, for a radioelement such as radium 224 or lead 212, to the purity this radioelement presents with regard to the radioelements from which it originates by radioactive decay, as well as with regard to the other radioelements which are not part of its radioactive decay chain, and not to the purity it presents with regard to the radioelements which it generates itself through its own radioactive decay.

In accordance with the invention, the liquid chromatography on a column is, preferably, carried out by using a stationary phase which selectively retains the lead 212 present in the aqueous solution A1 when this is contacted with the stationary phase, in other words which retains the lead 212 present in the aqueous solution A1 but which does not retain, or practically does not retain, the radiological and chemical impurities also present in this solution.

Moreover, the liquid chromatography on a column is, preferably, an extraction chromatography or a partition chromatography, in other words a chromatography which is based on the distribution of the elements that are to be separated between an organic phase, or extractant, and an aqueous phase, the extractant being bound to an inert support and forming with it the stationary phase, whereas the aqueous phase represents the mobile phase. Indeed, this type of chromatography has the advantage of combining the selectivity of the liquid-liquid extraction with the rapidity of the chromatography.

Within the scope of the invention, this extraction chromatography is advantageously carried out using a stationary phase which includes a crown ether as the extractant and, in particular, a dicyclohexano-18-crown-6 or a dibenzo-18-crown-6 whose cyclohexyl or benzyl groups are substituted by one or more $C_1$ to $C_{12}$ alkyl groups, with a straight or branched chain, in solution in an organic diluent not miscible with water, typically a long hydrocarbon chain alcohol, in other words a $C_8$ chain and above.

In particular, a stationary phase is used which comprises 4,4'(5')-di-tert-butylcyclohexano-18-crown-6 as the extractant, preferably diluted in octan-1-ol, such a stationary phase presenting the advantage of selectively retaining over 99% of the lead 212 present in an aqueous solution containing from 1.5 to 2.5 moles/L of a strong acid, which typically corresponds to the types of aqueous solutions that are used to extract lead 212 from a radium 224 generator.

This type of stationary phase is particularly available, in bottles but also packaged in ready-to-use columns or cartridges for chromatography, from the company TRISKEM International under the commercial name "Pb resin".

It is of course also possible to purify the lead 212 extracted from the generator by liquid chromatography on a column other than extraction chromatography, for example, cation exchange chromatography.

Whatever the type of liquid chromatography chosen and the type of stationary phase used, the liquid chromatography on a column preferentially comprises:
  loading the stationary phase with the aqueous solution A1, to allow the lead 212 present in this solution to be retained by the stationary phase;
  washing the stationary phase with an aqueous solution A2, to eliminate from the stationary phase the radiological and chemical impurities it contains but without eliminating the lead 212; then
  eluting the lead 212 from the stationary phase with an aqueous solution A3, to recover this lead in the form of an aqueous solution.

Evidently the conditions under which these three steps are carried out and, particularly, the pH values of aqueous phases A1, A2 and A3, are suitably chosen as a function of the stationary phase used.

Thus, for example, in the case where the liquid chromatography on a column is carried out using the previously mentioned "Pb resin" as the stationary phase:
  the aqueous solution A1 advantageously has an acidity corresponding to that of an aqueous solution of a strong acid having a molar concentration ranging from 1.5 to 2.5 and, preferably equal to 2, and corresponds, for example, to an aqueous solution containing from 1.5 to 2.5 moles/L and, even better, 2 moles/L of hydrochloric or nitric acid;
  the aqueous solution A2 advantageously has an acidity corresponding to that of an aqueous solution of a strong acid of molar concentration ranging from 0.1 to 0.5 and, preferably, equal to 0.5, and corresponds, for example, to an aqueous solution containing from 0.1 to 0.5 mole/L and, even better, 0.5 mole/L of hydrochloric or nitric acid; whereas
  the aqueous solution A3 advantageously has a pH ranging from 5 to 9 and corresponds, for example, to an aqueous solution of ammonium acetate which preferably contains 0.15 to 1 mole/L and, even better, 0.4 mole/L of ammonium acetate.

In accordance with the invention, the loading of the stationary phase with the aqueous solution A1 is carried out preferably without altering the pH that has this solution when it is extracted from the radium 224 generator.

Nevertheless, it is also possible to decrease (by addition of a strong acid) or increase (by dilution with water and/or addition of a strong base) the pH of the aqueous solution A1 before it is loaded onto the stationary phase present in the chromatography column in such a way that the retention of lead 212 by this stationary phase is optimal.

Advantageously, the method also comprises a bacteriological purification of the lead 212, which is preferably carried out after the liquid chromatography on a column, for example by circulating the aqueous solution having been used to elute the lead 212 through a 0.2 μm pore filter.

The production of the lead 212 in the radium 224 generator and its extraction from this generator can be carried out, in a manner known per se, by using as the solid medium a cation exchange resin that can retain the radium 224 but that does not retain the lead 212, for example the resin sold by the company BIO-RAD under the reference AG™ MP50 and which consists of a macroporous matrix of polystyrene/divinylbenzene onto which sulphonic groups —$SO_3H$ are grafted, and by:

- loading this resin with an acid aqueous solution containing radium 224, preferably of radiological purity greater than or equal to 99.5% such as, for example, an aqueous solution containing from 1 to 3 moles/L and, even better, 2 moles/L of hydrochloric or nitric acid;
- washing the resin with an aqueous acid solution, for example an aqueous solution containing from 0.01 to 2 moles/L and, even better, 0.01 mole/L of hydrochloric or nitric acid;
- leaving the radium 224 to produce lead 212 by radioactive decay; then
- eluting the resin with an aqueous acid solution, for example an aqueous solution containing from 1.5 to 2.5 moles/L and, even better, 2 moles/L of hydrochloric or nitric acid.

Preferably, the whole process is implemented within a closed system or circuit, that is to say in practice in an apparatus allowing all the aqueous solutions used or produced, from the aqueous solution used for extracting the lead 212 from the radium 224 generator to the aqueous solution containing the lead 212 eluted from the chromatography column, to circulate in a circuit that is totally isolated from the surrounding environment and, notably, from the ambient air and the pollutants contained therein, which contributes to obtaining lead 212 of very high chemical purity.

A subject-matter of the invention is also an apparatus specially designed for automated implementation in a closed system of the method as defined earlier, characterised in that it comprises at least:

- a generator comprising a solid medium onto which is fixed radium 224 to produce lead 212 by decay of this radium;
- means for extracting the lead 212 from the generator in the form of an aqueous solution A1;
- means for purifying the lead 212 contained in the aqueous solution A1 from the radiological and chemical impurities that this solution also contains by a liquid chromatography on a column;
- means for collecting the purified lead 212;
- means for a selective connection between the generator, the means for extracting the lead 212 from the generator, the means for purifying the lead 212 and the means for collecting the purified the lead 212; and
- an electronic processor for commanding the means for extracting lead 212 from the generator, the means for purifying the lead 212 and the means for the selective connection.

In accordance with the invention, the means for extracting the lead 212 from the generator advantageously comprise means for circulating an aqueous solution in the apparatus in order to circulate said aqueous solution in the generator, which means preferably comprise a first pump for drawing in the aqueous solution from the solution source and for injecting the drawn aqueous solution into the generator.

In addition, the means for purifying the lead 212 preferably comprise a chromatography column which contains a stationary phase capable of selectively retaining the lead 212 present in aqueous solution A1, when this is contacted with the stationary phase, as well as means for eluting the lead 212 from the stationary phase in the form of an aqueous solution.

In accordance with the invention, the means for eluting the lead 212 from the stationary phase advantageously comprise means for circulating an aqueous solution A3 in the apparatus in order to circulate said aqueous solution A3 in the chromatography column, which means preferably comprise a second pump for drawing in the aqueous solution A3 from the solution source and for injecting the drawn aqueous solution A3 into the chromatography column.

Advantageously, the first pump is able to draw in an aqueous solution A2 from the aqueous solution source and to inject the aqueous solution A2 into the chromatography column to wash the stationary phase.

The means for collecting the purified lead 212 preferentially comprise a flask in which the solution containing the lead 212 eluted from the stationary phase is collected.

Advantageously, the apparatus according to the invention further comprises a bacteriological purification filter which is placed between the flask and the chromatography column.

In a particularly preferred embodiment of the apparatus according to the invention, this comprises a chamber inside which the means for extracting the lead 212 from the generator, the means for purifying the lead 212 from the radiological and chemical impurities, the means for the selective connection and the electronic command processor are placed.

Preferably this chamber comprises means for connecting the apparatus to aqueous solution sources.

Also preferably, this chamber comprises a plurality of inlet ports each of which can be connected to an associated aqueous solution source, and the apparatus includes fail-safe means to prevent connecting an aqueous solution source to a port with which it is not associated.

The method and the apparatus which have just been described guarantee the production of lead 212 with a radiological purity at least equal to 99.95% and which can reach and even exceed 99.99%, and even 99.995%. To the best of the inventors' knowledge, lead 212 with such a high degree of radiological purity has never been obtained to date or, in any case, has never been described in the literature.

Another subject-matter of the invention is therefore lead 212 which has a radiological purity at least equal to 99.95%, preferably at least equal to 99.99% and, even better, at least equal to 99.995%.

Other characteristics and advantages of the invention will become apparent from the additional description given below with reference to the appended drawings.

This additional description is, of course, given for the purpose of illustration of the subject-matter of the invention only and in no case constitutes a limitation to this subject-matter.

DETAILED DESCRIPTION OF A SPECIFIC EMBODIMENT

Figure 1:
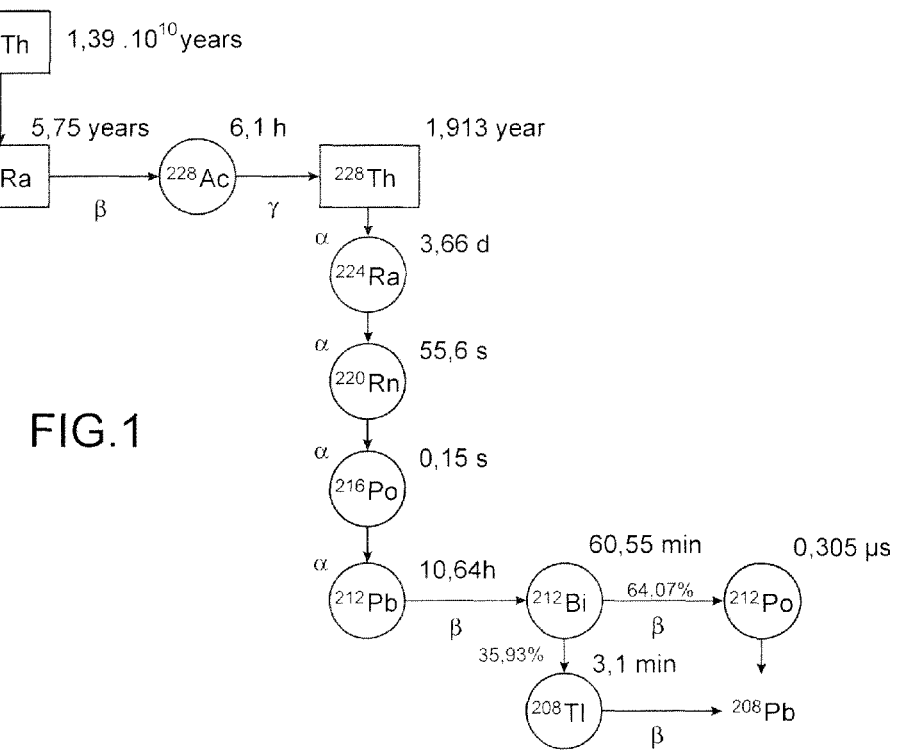
FIG. 1 represents the radioactive decay chain of thorium 232.
Figure 2:
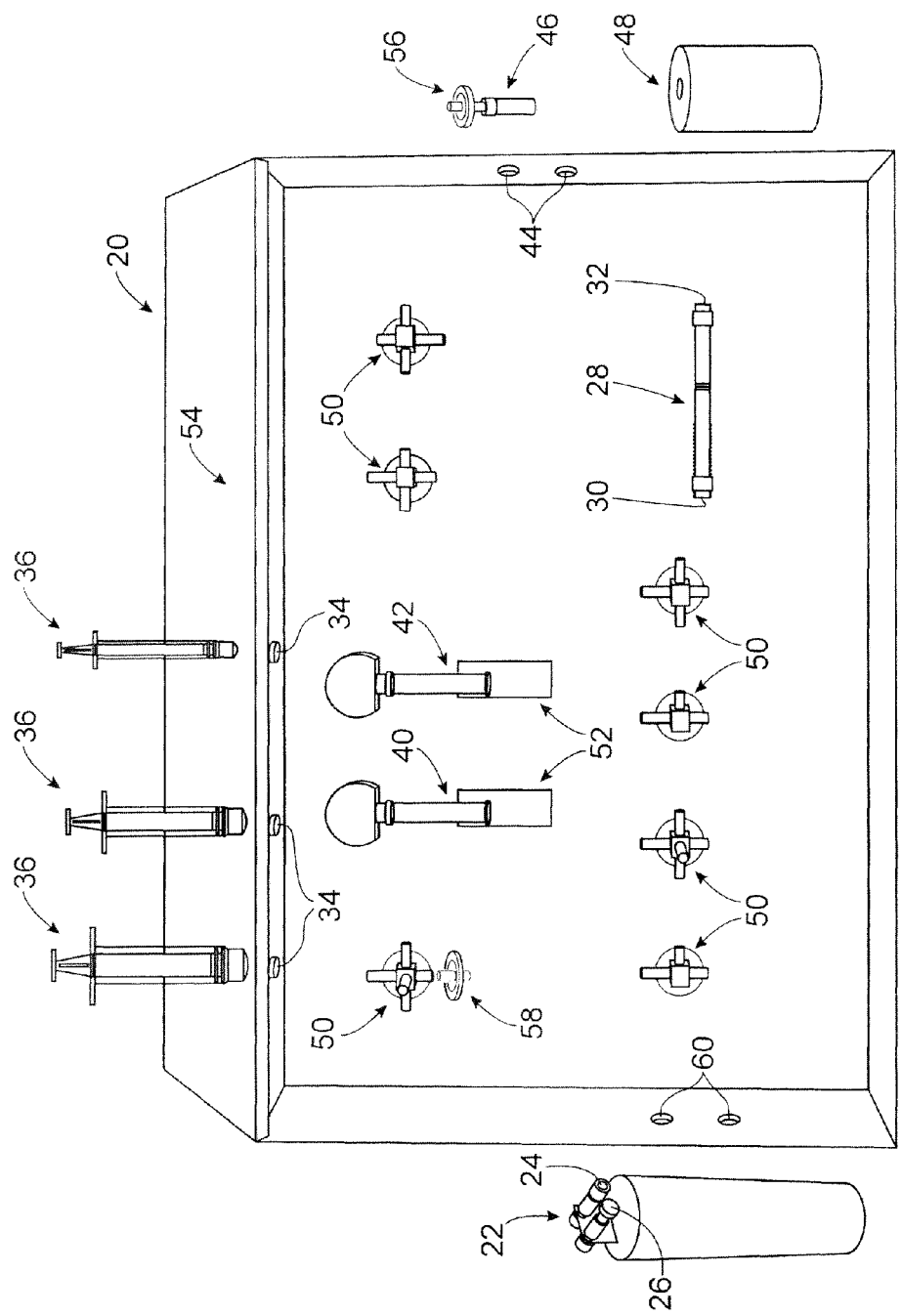
FIG. 2 is a diagrammatic representation of an example of an embodiment of the apparatus according to the invention.

This refers to FIG. 2 which diagrammatically represents an apparatus 20 according to the invention.

As can be seen from this figure, this apparatus firstly comprises a radium 224 generator 22 for the production of lead 212 by radioactive decay of this radium.

This generator consists of a device containing a solid medium, such as a cation exchange resin previously loaded with radium 224, this radium preferably having a radiological purity greater than or equal to 99.5%.

The generator 22 has two ports 24, 26, allowing it to be connected to the other components of the apparatus 20 by ducts (not represented).

This connection allows the lead 212 produced in the generator 22 to be extracted in the form of an aqueous solution.

The apparatus 20 also comprises a chromatography column 28 for purifying, by a liquid chromatography, the lead 212 extracted from the generator 22, from the radiological and chemical impurities which are extracted from this generator jointly with the lead.

This chromatography column can be either a column that has been previously prepared, conditioned and calibrated, or a commercially available ready-to-use column.

In all cases, it contains a stationary phase, such as an extraction chromatography stationary phase, which is capable of retaining lead 212 under certain conditions and also capable of releasing lead 212 by elution under other conditions.

The chromatography column 28 comprises a first port 30 and a second port 32 to connect it to the other components of the apparatus 20.

The apparatus 20 also comprises inlet ports 34 connecting it to the sources 36 of aqueous solutions.

According to a preferred embodiment particularly suited to the use of the apparatus 20 in a nuclear medicine department, each aqueous solution source 36 consists of a syringe filled with a predetermined amount of an appropriate aqueous solution which is to be used during the method. Each syringe 36 is suited to use in nuclear medicine: it has no rubber or silicon grease.

The apparatus 20 also comprises means for pumping 38 the various aqueous solutions contained in the syringes 36, in order to circulate the aqueous solutions in the generator 22 and in the chromatography column 28.

In the embodiment represented in FIG. 2, these pumping means 38 comprise two pumps 40 and 42, a first pump being employed to pump the aqueous solutions used respectively to extract the lead 212 from generator 22 and to wash the stationary phase contained in the chromatography column 28 after it is loaded with the aqueous solution used to extract the lead 212 from the generator 22, whereas the second pump 42 is employed to pump the aqueous solution used to elute the lead 212 from the chromatography column 28.

Preferably, each of the pumps 40 and 42 is of the syringe-pump type in order to pump an exact amount of aqueous solution.

The pumping means 38 also comprise two activators 52 each of which is associated with one of the two pumps 40 and 42 in order to drive this pump. These activators 52 can be electronically controlled to activate pumps 40 and 42 in a relatively precise manner in order to manage the quantity and flow of the pumped aqueous solutions.

The apparatus 20 also comprises outlet ports 44 to collect the aqueous solutions produced by the method according to the invention.

A first port 44 is connected to a flask 46 in which the aqueous solution containing the purified lead 212 is collected. A second port 44 opens into a receptacle 48 in which the other aqueous solutions are collected in order to be disposed of.

A filter 56 having, for example, a pore size of 0.2 vim is placed at the entrance to the flask 46 to complete the chemical purification of lead 212 by a bacteriological purification.

The apparatus 20 also comprises a plurality of multichannel valves 50 as well as a plurality of ducts (not represented) making it possible to selectively connect the components of the apparatus 20 one another for implementation of the method according to the invention.

The valves 50 can be electronically controlled in order to optimise circulation of the aqueous solutions in the apparatus 20.

The apparatus 20 also includes an electronic processor (not represented) for the command and control of the valves 50 and activators 52.

This processor makes it possible to automate the functioning of the apparatus 20, such that the manual operations then consist mainly of connecting certain components of the apparatus 20 prior to implementing the method of the invention and disconnecting these components at the end of the implementation.

The apparatus 20 still comprises a chamber 54 within which the chromatography column 28, the pumps 40 and 42, the activators 52, the valves 50 and, if need be, the electronic processor are placed. This chamber is presented here in the form of a parallelepiped in which the ports corresponding to the inlet ports 34 and outlet ports 44 of the apparatus 20 are found.

The chamber 54 preferably forms a sealed box preventing access to the elements it contains. The chamber also comprises means of access to its interior volume which can be locked. This makes it possible to prevent any non-qualified persons from accessing the components of apparatus 20, particularly the components having some radiological activity, or the components whose functioning can be damaged.

In the embodiment represented in FIG. 2, the radium 224 generator 22 is located outside the chamber 54. The latter therefore has two ports 60 which are crossed by pipes allowing the generator 22 to be connected to the other components of the apparatus 20.

The general dimensions of various components of the apparatus 20 are relatively small, which makes it possible to arrange them in a chamber 54 which is also small in size.

The apparatus 20 can therefore be a portable apparatus that can be used close to the area of usage of lead 212-based radiopharmaceuticals, for example in a nuclear medicine department.

As mentioned previously, the chamber 54 has several inlet ports 34 to which the different sources 36 of aqueous solution are connected to the apparatus. The sources 36 of the aqueous solutions are similar in nature and consist here of predosed syringes.

In order to guarantee the efficacy of the method according to the invention, each aqueous solution source 36 is associated with a single inlet port 34 through which the aqueous solution contained in this aqueous solution source supplies the apparatus.

In order to avoid any reversal between the aqueous solution sources, as a result of connecting a syringe to an inlet port 34 other than the inlet port 34 with which it is associated, the apparatus 20 comprises so-called failsafe means allowing an operator to correctly connect each aqueous solution source 36 to the inlet port 34 with which it is associated.

According to a first embodiment, the failsafe means are of a visual type and consist of colour coding, in other words labelling with a certain colour associated with each inlet port, and each aqueous solution source 36 has the same colour code as the one used to label the associated inlet port 34.

According to another embodiment, the failsafe means are mechanical in nature, in other words each inlet port 34 and the associated aqueous solution source have complementary shapes and sizes and the size and/or shape of an inlet port 34 and of the associated solution source 36 are different from the size and/or shape of another inlet port 34 and the associated solution source 36.

In this way it becomes impossible to connect a solution source 36 to an inlet port 34 with which it is not associated, thus preventing any human error.

According to a preferred embodiment of the apparatus 20, the generator 22 can be disconnected from the rest of the apparatus 20 to be replaced by another similar generator.

In fact, given that radium 224 has a half life of 3.66 days, the generator 22 can only be used for a limited period of time, usually for two weeks, after which the generator no longer contains a sufficient amount of radium 224. It therefore has to be replaced by a new generator.

In a similar manner, the chromatography column 28 can be disconnected from the rest of the apparatus 20 for replacement by another similar column.

The radium 224 generator 22 and the chromatography column 28 are both designed to allow the flow of aqueous solutions without manual intervention.

Thus by simply operating the valves 50 and activators 52 by means of the electronic processor, it is possible to circulate the different aqueous solutions from the syringes 36, in which the solutions are stored, through the generator and/or the chromatography column 28, and to direct these aqueous solutions towards the outlet ports of the apparatus 20, according to controlled flow rates.

The apparatus 20 thus makes it possible to implement the method of the invention in an automated manner.

In addition, the connections are all impermeable, which allows all the aqueous solutions circulating, from the syringes 36 to the flask 46 and to the receptacle 48, in a circuit that is totally isolated from the surrounding environment and, notably, from the ambient air and the pollutants contained therein.

The description which follows refers to an example of implementing the method according to the invention using the apparatus 20 which has just been described.

In this example, the syringes 36 are considered to be filled with an appropriate amount of an aqueous solution and are connected to the apparatus 20 as well as are the flask 46 and the receptacle 48.

Production of the Lead 212

The lead 212 is initially produced in the generator 22.

This production consists in leaving the radium 224 retained on the solid medium contained in the generator 22 to produce lead 212 by radioactive decay, for example over a period of one day.

Extraction of Lead 212

The lead 212 produced in the generator 22 is then extracted from this generator by elution, in other words by circulation in generator 22 of a first aqueous solution which draws out the lead 212 with it.

This extraction consists in taking the first aqueous solution, which is initially contained in a first syringe 36, by the first pump 40 then injecting it into the generator 22, also through this pump.

To do so, the valves 50 are directed by the electronic processor to connect the first pump 40 to the first port 24 of the generator 22.

Loading of the Stationary Phase of the Chromatography Column

The aqueous solution which leaves the generator 22 by the second port 26 of this generator contains lead 212, along with radiological and chemical impurities originating from the solid medium present in the generator 22.

This aqueous solution is taken directly into the chromatography column 28.

To do so, the valves 50 are adjusted to connect the second port 26 of the generator 22 to the first port 30 of the chromatography column 28.

The aqueous solution passes through the chromatography column 28. The lead 212 is retained by the stationary phase contained in this column while some of the radiological and chemical impurities remain in the aqueous solution and therefore leave the column 28 along with the aqueous solution.

Once it has left this column, the aqueous solution is directed towards the receptacle 48.

To do so, the valves are directed by the electronic processor to connect the second port 32 of the chromatography column 28 to the receptacle 48.

Washing of the Stationary Phase of the Chromatography Column

After being loaded, the stationary phase contained in the chromatography column 28 is washed with a second aqueous solution to extract the radiological and chemical impurities it contains from this phase but without extracting the lead 212.

This washing consists in taking the second aqueous solution, which is contained in a second syringe 36, by means of the first pump 40 then injecting it into the chromatography column 28, also through this pump.

The second aqueous solution then passes through the chromatography column 28, drawing with it the radiological and chemical impurities contained in the stationary phase, and is then directed towards the receptacle 48 in which it is collected.

To do this, the valves 50 are directed by the electronic processor to connect the first pump 40 to the first port 30 of the chromatography column 28 and to connect the second port 32 of the chromatography column 28 to the receptacle 48.

Elution of the Lead 212

The lead 212 retained by the stationary phase of the chromatography column 28 is then extracted from this column by elution, in other words by circulation in the chromatography column 28 of a third aqueous solution which draws out the lead 212 with it.

This elution consists in taking the third aqueous solution, which is contained in a third syringe 36, by the second pump 42 then injecting it into the chromatography column 28, also through this pump.

To do this, the valves 50 are directed by the electronic processor to connect the second pump 42 to the first port 30 of the chromatography column 28.

The third aqueous solution therefore passes through the chromatography column 28 drawing out the lead 212 with it.

A volume of aqueous solution leaving the chromatography column 28, which corresponds to the dead volume of the column, is initially directed towards the receptacle 48 in which it is collected.

To do this, the valves 50 are directed by the electronic processor to connect the second port 32 of the chromatography column 28 to the receptacle 48.

Next, the remaining aqueous solution leaving the chromatography column 28 is directed towards the flask 46 where it is collected after having passed through the filter 56.

To do this, the valves 50 are directed by the electronic processor to connect the second port 32 of the chromatography column 28 to the flask 46.

Apparatus Purging

According to a final step, the apparatus 20 is purged by circulating sterile air through it.

This sterile air is obtained by taking ambient air through the first pump 40 then passing this ambient air through a filter 58, having for example a pore size of 0.2 μm, which is placed to the air inlet.

Sterile air is then carried to the receptacle 48 to purge the circuit leading to this receptacle then up to the flask 46 to purge the circuit leading to this flask.

To do this, the valves 50 are directed by the electronic processor to connect the first pump 40 to the receptacle 48 then to the flask 46.

Lead 212 was produced with an apparatus similar to the one that has just been described and using:
- a radium 224 generator containing 400 mg of a cation exchange resin (company BIO-RAD—reference AG™ MP50) as the solid medium, this resin having been previously loaded with 10 mL of a solution containing 19 MBq of radium 224 of radiological purity greater than 99.5% (such as that determined by γ spectrometry) as well as 2 moles/L of hydrochloric acid (loading rate: 1 mL/min), then washed with 5 mL of an aqueous solution containing 0.01 mole/L of hydrochloric acid (washing rate: 1 mL/min);
- a ready-to-use chromatography column containing 80 mg of "Pb resin" (company TRISKEM International) as the stationary phase;
- 4 mL of an aqueous solution containing 2 mol/L of hydrochloric acid to extract the lead 212 from the generator and to load the stationary phase of the chromatography column (elution and loading rate: 1 mL/min);
- 2 mL of an aqueous solution containing 0.5 mole/L of hydrochloric acid to wash the stationary phase of the chromatography column (washing rate: 1 mL/min); and
- 1 mL of an aqueous solution containing 0.4 mol/L of ammonium acetate (pH 6.5) to elute the lead 212 from the stationary phase of the chromatography column (elution rate: 0.5 mL/min).

By leaving the radium 224 present in the generator 22 to produce lead 212 for 24 hours, 13 MBq of lead 212 were obtained, presenting:

(1) a radiological purity greater than 99.995%, as established from measurement of the radiological purity presented by this lead 212 after 10 decay periods, this measurement being carried out by means of a germanium detector;

(2) a chemical purity characterised by the presence, in the lead 212 elution solution, of:
- less than 11 ppb (parts per billion) of lead (other than lead 212);
- less than 2 ppb of vanadium, manganese, cobalt, copper, molybdenum, cadmium, tungsten and mercury;
- less than 20 ppb of iron; and
- less than 50 ppb of zinc;

(3) bacteriological purity characterised by sterility and less than 0.5 endotoxin unit/mL;

and this in less than 20 minutes between the start of the extraction of lead 212 from the radium 224 generator and the end of the filling of the flask 46 with purified lead 212.

For the purpose of comparison, the radiological purity (established under the same conditions) of the lead 212 produced by a method of the current state of the art ranges from 98 to 99.80%.

REFERENCES CITED

[1] Milanec et al., Cancer Biotherapy and Radiopharmaceuticals 2005, 20 (5), 557-568.
[2] Azure et al., World Molecular Imaging Congress, 8-11 Sep. 2010, Kyoto.
[3] Horak et al., Journal of Nuclear Medicine 1997, 38, 1944-1950.
[4] U.S. Pat. No. 4,663,129.

The invention claimed is:

1. A method for producing an aqueous solution of lead-212, comprising:
  (a) producing lead-212 by decay of radium-224 in a generator comprising a cation-exchange resin, wherein the radium-224 is bound to the resin;
  (b) eluting the lead-212 from the resin with a first aqueous solution comprising from 1.5 mol/L to 2.5 mol/L of a strong acid to form a second aqueous solution comprising the lead-212 and radiological and chemical impurities;
  (c) purifying the lead-212 from the radiological and chemical impurities by liquid chromatography on a column, the column comprising a stationary phase comprising 4,4'(5')-di-tert-butylcyclohexano-18-crown-6 in solution in an organic diluent not miscible with water, the liquid chromatography purification comprising:
    contacting the stationary phase with the second aqueous solution;
    washing the stationary phase with a third aqueous solution comprising from 0.1 mol/L to 0.5 mol/L of a strong acid; and
    eluting the lead-212 from the stationary phase with a fourth aqueous solution having a pH from 5 to 9 to form a fifth aqueous solution comprising the lead-212; and (d) submitting the fifth aqueous solution to a bacteriological purification to prepare the aqueous solution of lead-212.

2. The method of claim 1, wherein the first and third aqueous solutions are hydrochloric acid or nitric acid solutions.

3. The method of claim 1, wherein the fourth aqueous solution is an ammonium acetate solution.

4. The method of claim 3, wherein the fourth aqueous solution comprises from 0.15 mol/L to 1 mol/L of ammonium acetate.

5. The method of claim 1, wherein the bacteriological purification comprises circulating the fifth aqueous solution through a bacteriological filter.

6. The method of claim 1, further comprising collecting the aqueous solution of lead-212.

7. The method of claim 1, wherein the aqueous solution of lead-212 comprises less than 11 ppb of lead other than lead-212, less than 2 ppb of vanadium, manganese, cobalt, copper, molybdenum, cadmium, tungsten and mercury, less than 20 ppb of iron, and less than 50 ppb of zinc.

8. A method for producing an aqueous solution of lead-212 in an automated manner, comprising the steps of:
   (a) producing lead-212 by decay of radium-224 in a generator comprising a cation-exchange resin and wherein the radium-224 is bound to the resin;
   (b) eluting the lead-212 from the resin with a first aqueous solution comprising from 1.5 mol/L to 2.5 mol/L of a strong acid to form a second aqueous solution comprising the lead-212 and radiological and chemical impurities, the elution comprising drawing the first aqueous solution from a first solution source and injecting the first aqueous solution into the generator by a first pump;
   (c) purifying the lead-212 from the radiological and chemical impurities by liquid chromatography on a column, the column comprising a stationary phase comprising 4,4'(5')-di-tert-butylcyclohexano-18-crown-6 in solution in an organic diluent not miscible with water, and the liquid chromatography purification comprising:
      contacting the stationary phase with the second aqueous solution, the contacting comprising a circulation of the second aqueous solution from the generator to the column by means for connecting the generator with the column;
      washing the stationary phase with a third aqueous solution comprising from 0.1 mol/L to 0.5 mol/L of a strong acid, the washing comprising drawing the third aqueous solution from a second solution source and injecting the third aqueous solution into the column by the first pump; and
      eluting the lead-212 from the stationary phase with a fourth aqueous solution having a pH from 5 to 9 to form a fifth aqueous solution comprising the lead-212, the elution comprising drawing the fourth aqueous solution from a third solution source and injecting the fourth aqueous solution into the column by the first pump;
   (d) submitting the fifth aqueous solution to a bacteriological purification to prepare the aqueous solution of lead-212, the bacteriological purification comprising a circulation of the fifth aqueous solution from the column to a bacteriological purification filter by means for connecting the column with the bacteriological purification filter; and
   (e) collecting the aqueous solution of lead-212 in a flask, the collection comprising a circulation of the aqueous solution of lead-212 from the bacteriological purification filter to the flask by means for connecting the bacteriological purification filter with the flask;
wherein the first and second pumps, the means for connecting the generator with the column, the means for connecting the column with the bacteriological purification filter, and the means for connecting the bacteriological purification filter with the flask are commanded by an electronic processor.

9. The method of claim 8, wherein the first and third aqueous solutions are hydrochloric acid or nitric acid solutions.

10. The method of claim 8, wherein the fourth aqueous solution is an ammonium acetate solution.

11. The method of claim 10, wherein the fourth aqueous solution comprises from 0.15 mol/L to 1 mol/L of ammonium acetate.

12. The method of claim 8, wherein the aqueous solution of lead-212 comprises less than 11 ppb of lead other than lead-212, less than 2 ppb of vanadium, manganese, cobalt, copper, molybdenum, cadmium, tungsten and mercury, less than 20 ppb of iron, and less than 50 ppb of zinc.

* * * * *